US011457799B2

(12) United States Patent
Nadimi et al.

(10) Patent No.: US 11,457,799 B2
(45) Date of Patent: Oct. 4, 2022

(54) DUAL-MODE ENDOSCOPIC CAPSULE WITH IMAGE PROCESSING CAPABILITIES

(71) Applicants: SYDDANSK UNIVERSITET, Odense M (DK); REGION SYDDANMARK, Vejle (DK)

(72) Inventors: Esmaeil Shahrak Nadimi, Frederiksberg (DK); Gunnar Baatrup, Svendborg (DK); Claus Duedal Pedersen, Odense C (DK)

(73) Assignees: Syddansk Universitet; Region Syddanmark

( * ) Notice: Subject to any disclaimer, the term of this patent is extended or adjusted under 35 U.S.C. 154(b) by 20 days.

(21) Appl. No.: 16/956,720

(22) PCT Filed: Dec. 21, 2018

(86) PCT No.: PCT/EP2018/086609
§ 371 (c)(1),
(2) Date: Jun. 22, 2020

(87) PCT Pub. No.: WO2019/122338
PCT Pub. Date: Jun. 27, 2019

(65) Prior Publication Data
US 2020/0329955 A1    Oct. 22, 2020

(30) Foreign Application Priority Data
Dec. 22, 2017 (EP) .................................. 17210267

(51) Int. Cl.
*A61B 1/00* (2006.01)
*A61B 1/04* (2006.01)
(Continued)

(52) U.S. Cl.
CPC .......... *A61B 1/041* (2013.01); *A61B 1/00006* (2013.01); *A61B 1/00009* (2013.01); *A61B 1/0684* (2013.01); *G06N 20/00* (2019.01)

(58) Field of Classification Search
CPC ....... A61B 1/045; A61B 1/041; A61B 1/0638; A61B 1/0684; A61B 1/00006;
(Continued)

(56) References Cited

U.S. PATENT DOCUMENTS

2003/0174208 A1* 9/2003 Glukhovsky ........ H04N 5/2251
348/131
2006/0036131 A1* 2/2006 Glukhovsky ........ A61B 1/0638
600/160
(Continued)

FOREIGN PATENT DOCUMENTS

WO    2007105213 A2    9/2007
WO    2015072432 A1    5/2015

OTHER PUBLICATIONS

Dung et al., "A Wireless Narrowband Imaging Chip for Capsule Endoscope", IEEE Transactions on Biomedical Circuits and Systems, vol. 4, No. 6, Dec. 2010, pp. 462-468.
(Continued)

*Primary Examiner* — Timothy J Neal
*Assistant Examiner* — Sung Ham
(74) *Attorney, Agent, or Firm* — BakerHostetler (57) ABSTRACT

An endoscopic capsule comprising first and second imaging systems, wherein the first imaging system is arranged for obtaining images at a broader spectral range than the second imaging system, the capsule comprising a processor, the capsule arranged for operating in any one of a first mode wherein a frame rate of the first imaging system exceeds a frame rate of the second imaging system, and a second mode wherein the frame rate of the second imaging system
(Continued)

exceeds the frame rate of the second imaging system in the first mode, wherein the processor in the first mode is arranged for accessing one or more images from the first imaging system, detecting if there is a polyp in said one or more images, and switching from the first mode to the second mode if a polyp is detected in the one or more images from the first imaging system.

18 Claims, 2 Drawing Sheets

(51) Int. Cl.
     *G06N 20/00*           (2019.01)
     *A61B 1/06*            (2006.01)

(58) Field of Classification Search
     CPC ............ A61B 1/00181; A61B 1/00009; A61B 1/00016; A61B 1/00027; A61B 1/0661; A61B 5/6861; A61B 2562/0219; A61B 2562/0247; A61B 2562/162; G06N 20/00; H04N 1/21; H04N 1/2104; H04N 1/2108
     USPC .......................................................... 600/160
     See application file for complete search history.

(56) References Cited

U.S. PATENT DOCUMENTS

| | | | | |
|---|---|---|---|---|
| 2009/0240108 | A1* | 9/2009 | Shimizu | A61B 1/041 600/109 |
| 2011/0270057 | A1* | 11/2011 | Pascal | A61B 1/041 600/317 |
| 2012/0316421 | A1* | 12/2012 | Kumar | A61B 1/041 600/407 |
| 2014/0296666 | A1* | 10/2014 | Rabinovitz | A61B 5/0084 600/310 |
| 2015/0065850 | A1 | 3/2015 | Jia et al. | |
| 2015/0173623 | A1 | 6/2015 | Kostenich et al. | |
| 2016/0249793 | A1* | 9/2016 | Wang | A61B 1/31 600/109 |
| 2016/0353972 | A1* | 12/2016 | Yano | H04N 5/2256 |
| 2017/0127922 | A1* | 5/2017 | Godo | A61B 1/00158 |
| 2017/0265731 | A1* | 9/2017 | Yoshizaki | A61B 5/6861 |
| 2017/0296043 | A1* | 10/2017 | On | A61B 1/00036 |
| 2017/0304007 | A1 | 10/2017 | Piron et al. | |
| 2018/0365826 | A1* | 12/2018 | Oh | A61B 1/041 |
| 2020/0242764 | A1* | 7/2020 | Aoyama | A61B 1/00009 |

OTHER PUBLICATIONS

"PillcamTM System" The Gold Standard in Capsule Endoscopy, Medtronic, 2015, 6 pages.
Silva et al., "Towards Real-Time in Situ Polyp Detection in WCE Images Using a Boosting-Based Approach" Conf. Proc. IEEE Eng Med Biol Soc., 2013, 5 pages.
Schmidhuber, "Deep Learning in Neural Networks: An Overview", Neural Networks, vol. 61, Jan. 2015, pp. 85-117.
Misawa et al., "Artificial Intelligence-Assisted Polyp Detectionfor Colonoscopy: Initial Experience" Gastroenterology, vol. 154, 2018, pp. 2027-2029.
International Search Report and Written Opinion issued in PCT/EP2018/086609, dated Mar. 29, 2019.

* cited by examiner

DUAL-MODE ENDOSCOPIC CAPSULE WITH IMAGE PROCESSING CAPABILITIES

CROSS-REFERENCE TO RELATED APPLICATIONS

This application is the National Stage of International Patent Application No. PCT/EP2018/086609, "Dual-Mode Endoscopic Capsule with Image Processing Capabilities" (filed Dec. 21, 2018), which claims priority from EP Patent Application No. 17210267.5 (filed Dec. 22, 2017). The foregoing applications are incorporated herein by reference in their entireties for any and all purposes.

FIELD OF THE INVENTION

The present invention relates to an endoscopic camera and in particular relates to a dual-mode endoscopic capsule with image processing capabilities and a corresponding method and use.

BACKGROUND OF THE INVENTION

Early detection of colorectal cancer is relevant for enabling early treatment. Current screening programs, which include immunochemical fecal occult blood test (iF-OBT) and conventional optical colonoscopies, suffer from multiple shortfalls in sensitivity, specificity, risk, patient acceptance, availability and cost effectiveness.

Hence, an improved device and/or method for improving one or more of sensitivity, specificity, risk, patient acceptance, availability and cost effectiveness related to detection, such as early detection, of colorectal cancer would be advantageous.

SUMMARY OF THE INVENTION

It may be seen as an object of the present invention to provide a device and/or method for improving one or more of sensitivity, specificity, risk, patient acceptance, availability and cost effectiveness related to detection, such as early detection, of colorectal cancer. It is a further object of the present invention to provide an alternative to the prior art.

Thus, the above described object and several other objects are intended to be obtained in a first aspect of the invention by providing an endoscopic capsule comprising:
   a first imaging system,
   a second imaging system, wherein the first imaging system is arranged for obtaining images at a broader (such as at least 1% broader, such as at least 10% broader, such as at least 100% broader, spectral range than the second imaging system, and
   a processor, such as a processor arranged for image processing, such as image processing within the endoscopic capsule, such as a Central Processing Unit (CPU), such as a graphics processing unit (GPU), such as a Field-Programmable Gate Array (FPGA), such as an image only processing chip relying on deep learning,
wherein the endoscopic capsule is arranged for operating in any one of:
   a first mode wherein a frame rate of the first imaging system is higher than a frame rate of the second imaging system, and
   a second mode wherein the frame rate of the second imaging system is higher than the frame rate of the second imaging system in the first mode,
wherein the processor in the first mode is arranged for:
   accessing one or more images from the first imaging system,
   detecting if there is a polyp in the one or more images from the first imaging system, and
   switching from the first mode to the second mode if a polyp is detected in the one or more images from the first imaging system.

The invention may be particularly, but not exclusively, advantageous for obtaining an endoscopic capsule, which enables obtaining images with the second imaging system at a relatively high frame rate (in the second mode compared to the frame rate of the second imaging system in the first mode) when a polyp is detected (and thus likely in the field of view) and which enables operating the second imaging with a relatively low frame rate (in the first mode compared to the frame rate of the second system in the second mode) when no polyp is present. The endoscopic capsule may obtain images with the second imaging system when relevant and otherwise save energy.

The endoscopic capsule may enable increasing a frame rate of the second imaging system, with narrower spectral range than the first imaging system, if a polyp is detected by the first imaging system. This may be advantageous in that the power consuming second imaging system may then be activated only when it is possible to obtain images of polyps. This may in turn enable saving energy—which may be a limiting factor in an endoscopic capsule. Another possible advantage is that it enables that relatively few images are obtained with the second imaging system (e.g., as compared to an endoscopic capsule where a second imaging system obtains images at a constant frame rate), which may in turn be advantageous in that it enables transmitting all the obtained images. Another possible advantage may be that although the overall number of images obtained with the second imaging system may be relatively low (e.g., as compared to an endoscopic capsule where a second imaging system obtains images at a constant frame rate), the frame rate of images obtained when a polyp is present in front of the camera may be relatively high (e.g., as compared to an endoscopic capsule where the second imaging system obtains images at a constant frame rate, which may be relatively lower in order to ensure battery life time). The images obtained with the second imaging system may be obtained when—and only when—they are relevant.

In the context of the present invention, it is to be understood that when receiving a result of the invention, e.g., one or images from the secondary imaging system of a polyp, the resulting images may subsequently be the used in a decision process by a clinician or medically trained person, such as a gastroenterologist, resulting in a diagnosis, though the present invention does not necessarily comprises the intellectual step of making the diagnosis. It is contemplated that—at least part of—the decision process may be automated, e.g., as a part of a decision support system (DSS).

Additionally or alternatively, if one or more images from the secondary imaging system are potentially indicative of a disorder, a disease, and/or an abnormal condition, subsequent clinical actions or remedies may be initiated or recommended by a decision support system (DSS), e.g., such as if a polyp is potentially malicious and/or abnormal, such as being indicative of cancer, abnormal cell growth, a benign tumour, a malignant tumour, etc.

In general, a possible advantage may be that the present invention enables increasing the frame rate of the second imaging system, when a polyp is detected based on images from the first imaging system, which in turn enables that the second imaging system can be used for obtaining images at a relatively high frame rate (in the second mode as compared to the second imaging system in the first mode) when a polyp is present in the field of view of the endoscopic capsule (such as wherein images obtained with the second imaging system may be highly relevant) and be operated in a relatively low frame rate (in the first mode as compared to the second imaging system in the second mode)—and therefore with relatively low power consumption (in the first mode as compared to the second mode)—when no polyp is present (such as wherein the images may be irrelevant).

An advantage of saving energy by varying the frame rate of the second imaging system may be that only relatively few images (e.g., as compared to an endoscopic capsule where the second imaging system obtains images at a constant frame rate) are obtained with the second imaging system, and that there may be enough energy left for transmitting all these relatively few images, such as transmitting to external devices. This may in turn dispense with the need for collecting the endoscopic capsule after images have been obtained.

The endoscopic capsule may ensure good temporal resolution of the energy consuming second imaging system when a polyp is in the field of view of the capsule, but lower temporal resolution when no polyp is in the field of view (such as before a polyp is in the field of view). It might therefore be possible to overcome the necessity of making a trade-off between battery lifetime and temporal resolution (because the temporal resolution is sacrificed when it is irrelevant).

Another possible advantage e.g., with respect to colonoscopy, may be that embodiments of the endoscopic capsule may enable increasing accuracy, reducing false negatives and/or preventing a high number of colorectal cancer deaths that can be avoided by a proper on-time screening. A clinical trial (250 patients) has recently proven that an approach based on endoscopic capsules outperforms colonoscopy. Another possible advantage may be that embodiments of the present invention may enable reducing discomfort, risk of complications and/or adverse events for patients. Another possible advantage may be that embodiments of the present invention may enable increasing the likelihood that patients accept invitations to screening appointments, and keep the appointments. Another possible advantage may be that embodiments of the present invention may enable changing the screening process to reduce the level of expertise required at the Point-of-Care, opening-up new locations, safely, where screening can be offered—such as pharmacies and general practitioners (GPs) Another possible advantage may be that embodiments of the present invention may enable automating screening for both video capture and analysis, such as allowing experienced Gastroenterologists to spend more time on delivering diagnosis, treatment selection and performing necessary surgical interventions. Another possible advantage may be that embodiments of the present invention may enable reducing demand for high cost interventions, e.g., via increasing the early detection of disease because more people can be offered screening and a higher percentage attend screening and/or via improving, through the data and video collected by the endoscopic capsule, the precision of measurements, the ability to compare polyps with normalized data, and building risk associations accurately with known disease biomarkers. Another possible advantage, such as with respect to known endoscopic capsule without narrowband imaging capabilities and/or with limited battery life time being insufficient for obtaining the required images, may be that embodiments of the present invention may enable reducing the number of false-positives from screening, leading to fewer unnecessary treatments. In embodiments of the present invention, the battery life may exceed 8 hours, such as the battery life being 8.5 hours or more, such as 9 hours or more, such as 10 hours or more, such as 12 hours or more, such as 15 hours or more, such as 20 hours or more, such as 24 hours or more.

Another possible advantage may be that embodiments of the present invention may enable storing and analysing images/videos from endoscopic capsule (data repository) for adjacent use, such as by creating important disease and surgery insights from image analysis.

An 'endoscopic capsule' is understood as is common in the art, where it may also be referred to as a camera pill or a capsule camera. The term 'endoscopic capsule' may be understood as an independent and/or autonomous imaging entity of a limited volume, suitable for being swallowed by a normal human being. The capsule may be understood as a compact, particularly sealed, container or compartment. A length of the capsule (such as a maximum distance between any two points in the capsule) may be equal to or smaller than 5 centimetres, such as equal to or smaller than 4 centimetres, such as equal to or smaller than 3 centimetres, such as equal to or smaller than 2 centimetres, such as equal to or smaller than 1 centimetre, such as equal to or smaller than 0.5 centimetres. A volume occupied by the capsule (such as the volume enclosed in a fluid-tight packaging), may be equal to or smaller than 10 cubic centimetres, such as equal to or smaller than 5 cubic centimetres, such as equal to or smaller than 3 cubic centimetres, such as equal to or smaller than 2 cubic centimetres, such as equal to or smaller than 1.5 cubic centimetres, such as equal to or smaller than 1 cubic centimetre, such as equal to or smaller than 0.5 cubic centimetres.

By an 'imaging system' is generally understood a system enabling obtaining an image, such as a system comprising an optical system (such as an aperture and/or a lens) for making an image of an object, a media capable of storing an image, such as storing an image electronically (such as a complementary metal-oxide semiconductor (CMOS) sensor). The imaging system may furthermore comprise an illumination source. It might be understood that 'imaging arranged for obtaining images at a spectral range' may be understood functionally. It may in general be understood, that a plurality of imaging systems may share components, for example, the first and second imaging systems may share one or more of optical system and media capable of storing an image. It may be understood that an imaging system may comprise multiple field of views, e.g., a field of view as obtained from each end of the endoscopic capsule. In embodiments, the first and second imaging system may be given by, respectively, a first illumination source and a second illumination source, and then shared optical system, media capable of storing the image. Furthermore, the first and second imaging systems may share power sources. One or more of the shared components, may be shared temporally, such as the first imaging system obtains first images in a temporally limited period of time, then the second imaging system obtains first images in a temporally limited period of time, the first imaging system obtains first images in a temporally limited period of time, then the second imaging system obtains first images in a temporally limited period of time, and so forth.

It may be understood, that any imaging system is arranged for obtaining images at a certain spectral range. The selection of spectral range may be realized in a number of ways, e.g., by illuminating with a certain spectral range (and having optical system and media capable of storing an image with spectral ranges encompassing said certain spectral range), by inserting a filter with a certain spectral range (and having illumination, optical system and media capable of storing an image with spectral ranges encompassing said certain spectral range), and combinations of the above (e.g., having an upper limit of the certain spectral range set by an upper limit of illumination and a lower limit of the certain spectral range set by a lower limit of the media capable of storing an image or vice versa).

By "spectral range" of an imaging system may be understood full-width at half max (FWHM) of a peak in the spectrum of the imaging system if only one peak is present or as a distance between the most distant peaks (as measured between the most distant part of the respective peaks at the half max intensity of the smallest intensity peak) if multiple peaks are present (such as wherein peaks having an intensity of less than $1/3$, such as $1/5$, such as $1/10$, of the peak with the maximum intensity may be disregarded).

By "arranged for obtaining images at a broader spectral range" may be understood that a spectral range of the first imaging system is larger than a spectral range of the second imaging system.

A 'processor' is understood as is common in the art, such as a processing unit being an electronic circuit which performs operations on some external data source, usually memory or some other data stream. It may be a processor arranged for image processing, such as image processing within the endoscopic capsule. The processor may be a Central Processing Unit (CPU), a graphics processing unit (GPU), a Field-Programmable Gate Array (FPGA) or an image only processing chip relying on deep learning. A possible advantage of having the processor being an FPGA may be that it provides more processing power and/or higher flexibility while achieving lower power consumption compared to, e.g., microcontrollers. This may be advantageous, e.g., for satisfying hardware requirements for exploiting advanced machine learning and pattern recognition algorithms running on the processor within the endoscopic capsule.

The endoscopic capsule may be operated in a plurality of modes, including a first mode and a second mode, such as operated in exactly one of a finite number of states at any given time. It can change (in a transition) from one state to another in response to some external inputs.

In a 'first mode' a frame rate of the first imaging system is higher than a frame rate of the second imaging system. A possible advantage of this may be that in the first mode, the first imaging system can obtain images with a relatively high temporal resolution (as compared to the temporal resolution of the energy consuming second imaging system in the first mode), which images can be used for detection of polyps.

In a 'second mode' the frame rate of the second imaging is higher than the frame rate of the second imaging system in the first mode. This may be advantageous for having a higher frame rate when it is relevant (when a polyp is detected), and a lower frame rate when it is not relevant (when a polyp is not detected, such as before a polyp is detected in the field of view and optionally after a polyp is no longer detected in the field of view).

By 'frame rate' is understood the rate with which images (frame) are obtained, such as 1 frame per second (fps), such as 2 fps, such as 4 fps, such as 8 fps, such as 16 fps, such as 32 fps, such as 64 fps.

The processor is in the first mode is arranged for accessing one or more images from the first imaging system and detecting, such as via assessing the one or more images from the first imaging system, such as via image analysis of the one or more images from the first imaging system, if there is a polyp in the one or more images from the first imaging system. It may be understood, that the detecting if there is a polyp in the one or more images from the first imaging system is carried out within a timescale after obtaining said images, which allows obtaining images of substantially the same field of view, such as of a polyp in the one or more images, such as of the same field of view, as in said one or more images obtained with the first imaging system, such as in a period of time being equal to or less than 10 seconds, such as equal to or less than 5 seconds, such as equal to or less than 2 seconds, such as equal to or less than 1 seconds, such as equal to or less than 0.5 seconds, such as equal to or less than 0.1 seconds, such as equal to or less than $1/32$ seconds, such as equal to or less than $1/64$ seconds.

The processor is in the first mode furthermore arranged for switching from the first mode to the second mode if a polyp is detected in the one or more images from the first imaging system. This may correspond to a transition in a state machine. An advantage may be that the switching (or the transition) is the result of detection on a polyp in the field of view, thus entry into the second mode may happen exactly when—and only when—it is relevant. This may ensure optimal usage of the second image system and battery life. Detection may be carried out via colour-based segmentation algorithms optionally combined with texture estimation-based techniques for autonomous pattern recognition of polyps.

In an embodiment there is presented an endoscopic capsule wherein the endoscopic capsule is further arranged for transmitting (such as wirelessly transmitting) images outside the endoscopic capsule from the first and/or second mode (such as images from the second mode and images from the first mode, such as images from the second mode and corresponding images from the first mode where corresponding implies that the images are obtained at substantially the same time, such as at the same time), such as wherein a polyp is detected, such as arranged for only transmitting images wherein a polyp is detected. An advantage of this may be that relevant images, such as all relevant images and/or only relevant images are transmitted. This may ensure optimal usage of the power for transmitting and battery life. It may be understood that images from the second mode may comprise both images from the first imaging system and the second imaging system. An advantage of having transmitting images from the first imaging system and the second imaging system may be that it enables a person or system receiving these images to perform an improved analysis (with respect to a situation wherein only images from the first mode or the second mode were transmitted). Transmission may take place via an RF transmitter and an RF antenna in the endoscopic capsule. In embodiments, the endoscopic capsule comprises an RF transmitter and an RF antenna. By '(transmitting) outside the endoscopic capsule' is understood that data comprising the images may be obtained by an entity, such as a receiver, outside of the capsule.

In an embodiment there is presented an endoscopic capsule wherein the first imaging system is a white light imaging system. The 'first imaging system' may in particular embodiments be a white light (WLI) imaging system. White light is understood as is known in the art. An advantage of this may be that white light images may be obtained, which may enable colour-based segmentation of polyps. Colour-based segmentation may overcome problems related to detection of polyps based on some measure of protrusions from the surrounding mucosal tissue, use of principal curvatures and the related quantities, such as shape index and curvedness and/or the radius of the best-fit ball fit. Polyps are more vascularized compared to the inner lining of the gastrointestinal (GI) tract and therefore colour-based segmentation algorithms optionally combined with texture estimation-based techniques for autonomous pattern recognition of polyps seems a better choice as a solution. In particular embodiments, white light may refer to a spectral range spanning (such as continuously spanning, such as having a single peak spanning) at least 150 nm, such as at least 200 nm, such as at least 300 nm, within a range of electromagnetic radiation with a wavelength between 380 nm and 760 nm (400-790 terahertz), which is detected by the human eye and perceived as visible light.

In an embodiment there is presented an endoscopic capsule wherein the second imaging system is a narrowband imaging system. The 'second imaging system' may be referred to as a narrowband imaging system (where it is understood that 'narrow' is relative to the first imaging system in that the second imaging system is arranged for obtaining images at a narrow spectral range with respect to the first imaging system). An advantage of this may be that it enables distinguishing between non-neoplastic and neoplastic polyps (which may reduce a rate of false positives, which may in turn reduce a burdening of the endoscopy units). More particularly: According to the basics of physics, the penetration depth of light depends on its wavelength.

The choice of narrowband imaging (NBI) spectra may be based on the light absorption property of haemoglobin. Thus, the microvasculature of the mucosal surface can be clearly seen as dark traces, which enables gastroenterologists to distinguish neoplastic polyps from the non-neoplastic ones. This information combined with the histological properties of the polyps and their estimated size and shape are ultimate indicators of polyp malignancy stage.

In particular embodiments, narrowband may refer to a spectral range spanning at most 100 nm, such as at most 50 nm, such as at most 25 nm, optionally within a range of electromagnetic radiation with a wavelength between 380 nm and 760 nm. The 'second imaging system' may in particular embodiments have a spectral range with a centre wavelength in any one the ranges 415 (+/−30) nm, 445 (+/−30) nm or 500 (+/−30) nm.

In embodiments, the endoscopic capsule may furthermore comprise a third imaging system (e.g., in addition to an imaging system operating within a green narrowband spectral range there may be an imaging system operating within a blue narrowband imaging range), which is operated with a frame rate similar to the frame rate of the second imaging system. The third imaging system may be referred to as narrowband imaging system. The third imaging system may in particular embodiments have a spectral range with a centre wavelength in any one the ranges 415 (+/−30) nm, 445 (+/−30) nm or 500 (+/−30) nm. The third imaging system may in particular embodiments have a centre frequency which is different with respect to a centre wavelength of the second imaging system, such as separated by at least 10 nm, such as separated by at least 20 nm, such as separated by at least 50 nm, such as separated by at least 100 nm.

The first, second and/or the third imaging system may comprise LED illumination and/or a colour filter array.

In an embodiment there is presented an endoscopic capsule comprising one or more illumination systems, such as an illumination system comprising a white light source and a narrowband imaging source, such as an illumination system comprising 6 light emitting diodes including 2 white light emitting diodes and 2 green light emitting diodes and 2 blue light emitting diodes. An advantage of having one or more illumination systems may be that they enable obtaining images when little or no light is present, such as within the body. Another advantage of having one or more illumination systems may be that it enables setting the spectral range of first and/or second (and/or third) imaging system, such as wherein a first and second illumination system, respectively, defines the spectral range of the first and second imaging system. A possible advantage of having green and blue light emitting diodes may be that they spectrally match light absorption peaks in haemoglobin.

In a specific embodiment, the first- and second imaging systems are as described in the reference, such as in FIG. 4 and the accompanying text of the reference, "*A Wireless Narrowband Imaging Chip for Capsule Endoscope*", by Lan-Rong Dung in IEEE TRANSACTIONS ON BIOMEDICAL CIRCUITS AND SYSTEMS, VOL. 4, NO. 6, DECEMBER 2010, which reference is hereby incorporated by reference in entirety, and in particular FIG. 4 and the accompanying text of the reference is included by reference.

In an embodiment there is presented an endoscopic capsule wherein the processor is arranged for employing a machine learning algorithm for detecting if there is a polyp in the one or more images from the first imaging system. An advantage of this may be that machine learning algorithms may be superior for detection of polyps in images. The machine learning algorithm may rely on colour-based segmentation algorithms. Such algorithms have been in skin detection for gesture recognition problems. Generally, polyps are more vascularized compared to the inner lining of the gastrointestinal (GI) tract and therefore colour-based segmentation algorithms optionally combined with texture estimation-based techniques for autonomous pattern recognition of polyps seems an optimal choice. The inventors have employed machine learning algorithms trained on a set of 3000 images, which algorithm obtains 94% accuracy, 94% sensitivity and 98% specificity. The images may be adapted to have a certain set of properties to be fitted to the network, if the original size of the images is totally different from what the network accepts. There may be pre-processing to be done: normalization, centring and/or removing artefacts. The network can have a variable size between 16 to 177 layers where the last 3 layers are solely designed for the problem in hand (i.e., polyp detection).

'Machine learning algorithm' is understood as is common in the art. 'Machine learning algorithm' may be understood an algorithm that provides a system the ability to automatically learn and improve from experience without being explicitly programmed and/or an algorithm that has accessed data and used it to learn for itself and/or an algorithm that can access data and use it learn for itself. Machine learning algorithms are known in the art and described in for example the reference "*Deep Learning in Neural Networks: An Overview*", by Jurgen Schmidhuber in Neural Networks, Volume 61, January 2015, Pages 85-117, which reference is hereby incorporated by reference in entirety. An example of a specific algorithm is presented in the reference US 201510065850 A1, which reference is hereby incorporated by reference in entirety. Another example of a specific algorithm is presented in the reference "*Towards real-time in situ polyp detection in WCE images using a boosting-based*

*approach*", by Silva J, Histace A, Romain O, Dray X, Granado B, and Pinna A., in Conf Proc IEEE Eng Med Biol Soc. 2013; 2013:5711-4, which reference is hereby incorporated by reference in entirety. Another example of a specific algorithm is presented in the reference "Artificial Intelligence-Assisted Polyp Detection for Colonoscopy: Initial Experience", by Masashi Misawa, Shin-ei Kudo, Yuichi Mori, Tomonari Cho, Shinichi Kataoka, Akihiro Yamauchi, Yushi Ogawa, Yasuharu Maeda, Kenichi Takeda, Katsuro Ichimasa, Hiroki Nakamura, Yusuke Yagawa, Naoya Toyoshima, Noriyuki Ogata, Toyoki Kudo, Tomokazu Hisayuki, Takemasa Hayashi, Kunihiko Wakamura, Toshiyuki Baba, Fumio Ishida, Hayato Itoh, Holger Roth, Masahiro Oda and Kensaku Mori., in Gastroenterology, 2018; 154: 2027-2029, which reference is hereby incorporated by reference in entirety.

The group of inventors have conducted a study regarding their machine learning algorithm, a deep convolutional neural network (CNN) used in the present invention. The study compares other types of machine learning algorithms for the finding and identification of colorectal polyps obtained during wireless colon capsule endoscopy. The study documents the advantageous effects of using their machine learning algorithm for identifying polyps from wide-band images before the present invention automatically switching to the second imaging system in the second mode and hereafter obtaining additional images at an energy-consuming narrow-band mode for improved diagnosis and investigation of colon pathology—see Table 1 for details regarding the performance of the inventors CNN compared to existing machine learning algorithms.

TABLE 1

Performance of different networks on training and vaidation dataset.

| Network | Accuracy % | Sensitivity % | Specificity % |
|---|---|---|---|
| Invention CNN | 98.0 | 98.1 | 96.3 |
| AlexNet | 74.1 | 92.3 | 82 |
| GoogleNet | 51.2 | 13.2 | 99.4 |
| ResNet50 | 69.7 | 80.7 | 99.3 |
| VGG16 | 63.5 | 42.4 | 85.6 |
| VGG19 | 82.7 | 68.8 | 90.2 |

In an advantageous embodiment of the present invention, the endoscopic capsule further comprises a receiver for Over The Air Programming (OTAP), such as a wireless receiver, for receiving instruction from outside the capsule.

In a more advantageous embodiment of the present invention, the instructions received may be machine learning algorithms for detecting a specific pathology, such as a polyp, in an image obtained in the one or more images from the first imaging system.

In an embodiment there is presented an endoscopic capsule wherein the endoscopic capsule is arranged so that a period of time covering (such as spanning):
  obtaining (in the first mode) with the first imaging system an image with a polyp,
  detection of a polyp in the image with the polyp,
  switching from the first mode to the second mode due to the detection of the polyp in the image with the polyp, and
  obtaining (in the second mode) with the second imaging system an image, such as obtaining with the second imaging system an image of the polyp, is equal to or less than 10 seconds, such as equal to or less than 5 seconds, such as equal to or less than 2 seconds, such as equal to or less than 1 seconds, such as equal to or less than 0.5 seconds, such as equal to or less than 0.1 seconds, such as equal to or less than $\frac{1}{32}$ seconds, such as equal to or less than $\frac{1}{64}$ seconds. An advantage of this may be that said period of time is within a timescale, which allows obtaining one or more images with the second imaging system in the second mode of substantially the same field of view and/or of a polyp in the one or more images, such as of the same field of view, as in said one or more images obtained with the first imaging system in the first mode.

In an embodiment there is presented an endoscopic capsule wherein the processor in the second mode is arranged for:
  accessing one or more images from the first imaging system and/or the second imaging system,
  detecting and/or confirming if there is a polyp in the one or more images from the first imaging system and/or the second imaging system, and
  the processor is furthermore arranged for switching from the second mode to the first mode, such as switching back from the second mode to the first mode, if a polyp is not detected in the one or more images from the first imaging system.

An advantage of this may be that it ensures that after detection of a polyp, and after the system has been switched into the second mode (which may be more energy consuming than the first mode), the endoscopic capsule can return to operating in the first mode (which may be less energy consuming than the second mode).

In an embodiment there is presented an endoscopic capsule wherein the endoscopic capsule is also arranged for quantifying bowel cleanliness. An advantage of this may be that it enables determining unambiguously when bowel cleanliness is insufficient, such as insufficient in terms of detecting and/or assessing polyps. In an embodiment, endoscopic capsule is arranged for quantifying bowel cleanliness via a machine learning-based model to classify bowel cleansing quality. Bowel cleanliness may be classified as unacceptable, poor, fair or good. In an embodiment, endoscopic capsule is arranged for quantifying bowel cleanliness via support Vector Machines (SVM), which are based on machine learning concepts, in which expert's input is used to train the model to classify a variable. In a study featuring inventors of the present application, SVM was used to determine the cleanliness of a pixel. A medical doctor classified pixels to be either clean or dirty in a random selection of endoscopic capsule images (frames). The model based on this data made a clear distinction between the dirty and clean pixels. The next step was to determine the cleanliness of an image (video frame), based on the number of clean and dirty pixels. Pixels that were over or underexposed in the image (frame) were excluded for this analysis. The cleanliness was subsequently assessed by the following equation (equation (3)), in which $N_A$ is the number of classified pixels per image (frame) and $f(d_i)$ represents the cleanliness of one pixel using SVM algorithms as described below.

$$I_k = \frac{1}{N_A}\sum_{i=1}^{N_A} f(d_i) \tag{3}$$

In this study, a nonlinear classification is applied with a Gaussian radial basis function as kernel. Further, the pixel classification function f($d_i$) in Eq. (3) is modified to resemble a soft transition between dirty and clean pixels. By defining d_i. as the distance between the $i^{th}$ pixel to the hyperplane in the RGB feature space, where the sign represents whether the pixel is clean or dirty, the function f($d_i$) determines the cleanliness of the pixel as follows:

$$f(d_i) = \begin{cases} -1 & \text{if } d_i \leq -\alpha \\ \frac{1}{\alpha} d_i & \text{if } -\alpha < d_i < \alpha \\ 1 & \text{if } \alpha \leq d_i \end{cases} \quad (4)$$

Applying Eq. (4) to the pixels in the vicinity of the hyperplane with radius 0, the cleanliness is determined based on the distance of the point to the hypersphere. The points outside a have binary cleanliness.

As Eq. (3) returns a continuous variable, the cleanliness of an image (frame) is evaluated by comparing $I_k$ to a series of thresholds given by:

$$L^j = \begin{cases} 0 \text{ (Unacceptable)} & \text{if } T_1 < I_k \leq 1 \\ 1 \text{ (Poor)} & \text{if } T_2 < I_k \leq T_1 \\ 2 \text{ (Fair)} & \text{if } T_3 < I_k \leq T_2 \\ 3 \text{ (Good)} & \text{if } -1 \leq I_k \leq T_3 \end{cases} \quad (5)$$

As the SVM classifier is trained on domain knowledge, there are no free parameters in the cleanliness assessment. However, the parameters in Eqs. (4) and (5), namely α, and $T_k$, k=1, 2, 3 are estimated through an optimization process.

In order to define and solve the optimization problem at hand, a gold standard is necessary. For this purpose, a variety of colon images (frames) from different patients and different cleanliness levels are selected. The cleanliness of images (frames) is assessed by a medical doctor. Finally, a set of $N_g$ assessed images (frames) is selected:

$$L_g^j; j=1,2,\ldots,N_g. \quad (6)$$

The parameters can be estimated by solving $$\min \sum_{j=1}^{N_g} |E^j| = \min \sum_{j=1}^{N_g} |L_g^j - L^j| \quad (7)$$

where $E^J$ is the estimated error of the image's (frame's) cleanliness.

In an embodiment there is presented a system comprising:
the endoscopic capsule,
an optional database of machine learning algorithms suitable for transmitting one or more machine learning algorithms to the endoscopic capsule, and
a database suitable for storing images obtained in the second mode.

An advantage of this may be that the database may enable secure storage of the images obtained with the endoscopic capsule. Another possible advantage may be that images in the database may enable improving algorithms for polyp detection and/or characterization.

In an embodiment there is presented a kit comprising:
the endoscopic capsule, such as wherein the endoscopic capsule comprises an RF transmitter and an RF antenna,
an optional transmitter for transmitting one or more instructions, such as machine learning algorithms to the endoscopic capsule, and
a receiver with one or more antennas, such as an RF receiver with an RF antenna, such as a receiver with an antenna for receiving information (such as images) sent from the endoscopic capsule via the RF transmitter and the RF antenna in the endoscopic capsule, arranged for receiving images from said endoscopic capsule.

In a further embodiment, the kit furthermore comprises a clear liquid, such as a bowel preparation liquid.

According to a second aspect there is presented a method of operating an endoscopic capsule, such as a pre-delivered (such as pre-swallowed) endoscopic capsule, wherein said method comprises:
operating the endoscopic capsule in the first mode,
obtaining one or more images with the first imaging system,
accessing with the processor the one or more images from the first imaging system,
detecting if there is a polyp in the one or more images from the first imaging system, and
switching from the first mode to the second mode if a polyp is detected in the one or more images from the first imaging system.

In an embodiment there is presented a method of operating an endoscopic capsule wherein the method further comprises, such as wherein the method prior to obtaining one or more images with the first imaging system further comprises, swallowing the endoscopic capsule.

In an embodiment there is presented a method of operating an endoscopic capsule wherein the method further comprises:
operating 238 the endoscopic capsule in the second mode,
obtaining 240 one or more images 242 with the first imaging system,
accessing 244 with the processor the one or more images 242 from the first imaging system, such as accessing and image analysing so as to obtain a quantification of likelihood 245 that the image comprises a polyp 104,
detecting 246 if there is a polyp 104 in the one or more images from the first imaging system, such as determining if the likelihood 245 is above a predetermined threshold, and
switching 248 from the second mode to the first mode if a polyp 104 is not detected in the one or more images from the first imaging system.

In an embodiment there is presented a method of operating an endoscopic capsule wherein the method further comprises,
operating the endoscopic capsule in the second mode,
obtaining one or more images with the second imaging system and optionally with the first imaging system (such as in the second mode), and
transmitting one or more images (such as images obtained with the first and/or second imaging system) obtained in the second mode to a database.

In an embodiment there is presented a method of operating an endoscopic capsule according the second aspect, wherein the method further comprises transmitting one or more instructions, such as machine learning algorithms to the endoscopic capsule prior to the any of the preceeding steps.

According to third aspect there is presented a use of an endoscopic capsule according to the first aspect for obtaining a set of a plurality of images from any of the first and second image systems and/or first and second modes and optionally for transmitting a subset of said set of a plurality of images.

The first, second and third aspect of the present invention may each be combined with any of the other aspects. These and other aspects of the invention will be apparent from and elucidated with reference to the embodiments described hereinafter.

BRIEF DESCRIPTION OF THE FIGURES

The first, second and third aspect according to the invention will now be described in more detail with regard to the accompanying figures. The figures show one way of implementing the present invention and is not to be construed as being limiting to other possible embodiments falling within the scope of the attached claim set.

DETAILED DESCRIPTION OF AN EMBODIMENT

Figure 1:
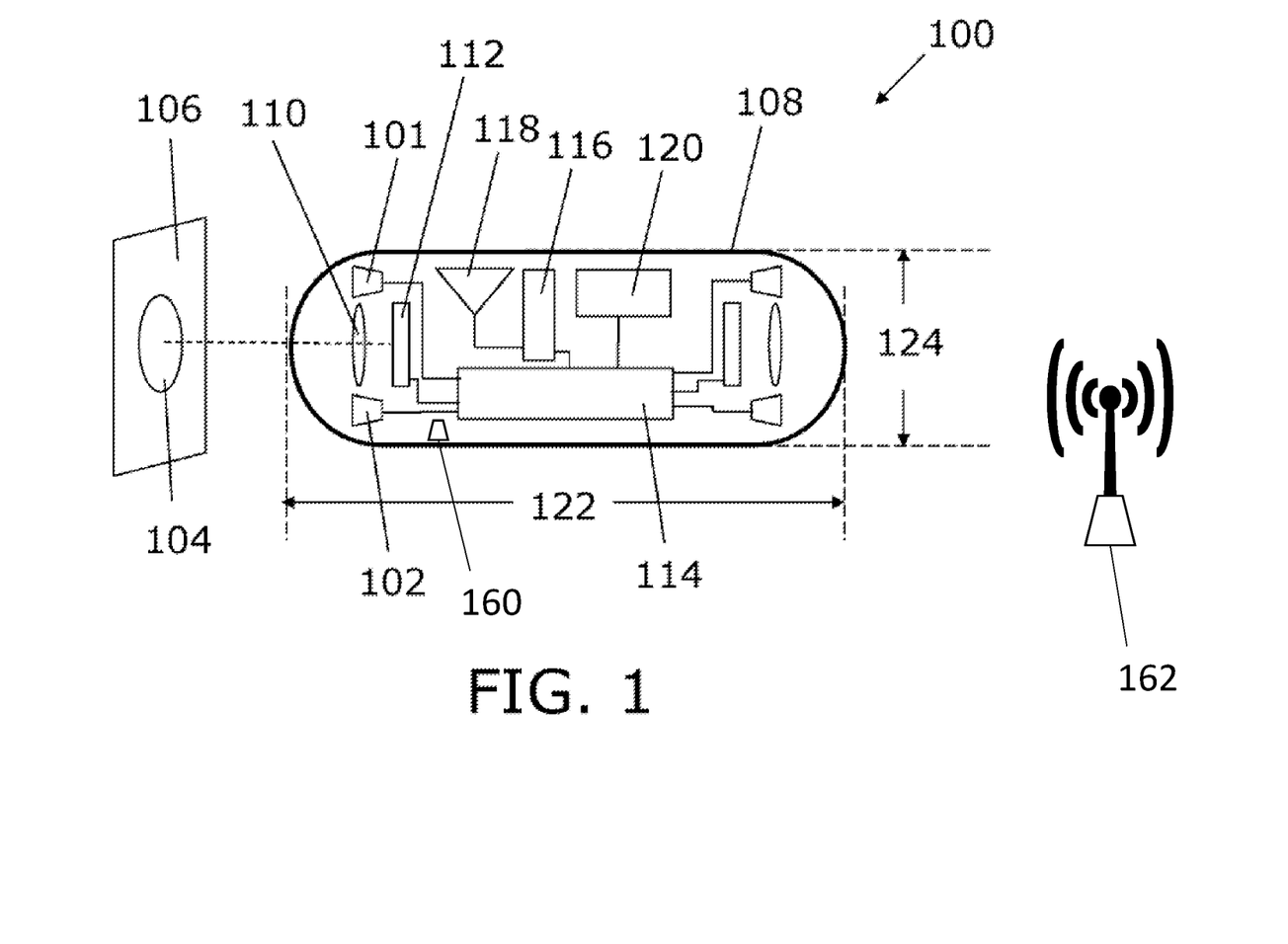
FIG. 1 shows a schematic of an endoscopic capsule according to an embodiment of the invention.

FIG. 1 shows a schematic of an endoscopic capsule according to an embodiment of the invention. More particularly, the figure shows an endoscopic capsule 100 comprising:
- a first imaging system, such as a first imaging system comprising a white light emitting diode (LED) 101, refractive lens 110 and two-dimensional image sensor 112 with colour filter array, and
- a second imaging system, such as a second imaging system comprising a blue light emitting diode (LED) 102, refractive lens 110 and two-dimensional image sensor 112 with colour filter array (note that the refractive lens 110 and two-dimensional image sensor 112 with colour filter array is shared with the first imaging system).

The endoscopic capsule 100 according to the present embodiment furthermore comprises
- a third imaging system, such as a third imaging system comprising a green LED (not shown), a refractive lens 110 and a two-dimensional image sensor 112 with a colour filter array.

The first imaging system is arranged for obtaining images at a broader spectral range than the second imaging system.

The endoscopic capsule 100 according to the present embodiment furthermore comprises
a processor 114 being an FPGA,
wherein the endoscopic capsule is arranged for operating in any one of:
- a first mode wherein a frame rate (such as 1-32 fps) of the first imaging system is higher than a frame rate (such as 0 fps) of the second imaging system, and
- a second mode wherein the frame rate (such as 1-32 fps) of the second imaging system is higher than the frame rate (such as 0 fps) of the second imaging system in the first mode.

The frame rate of the first imaging system in the second mode may be 1-32 fps. The processor (114) in the first mode is arranged for:
accessing one or more images from the first imaging system,
detecting if there is a polyp 104, such as a polyp on the inner lining 106 of the colon, in the one or more images from the first imaging system, and
switching from the first mode to the second mode if a polyp 104 is detected in the one or more images from the first imaging system.

The endoscopic capsule 100 according to the present embodiment comprises imaging systems in both ends. This may decrease a risk that a polyp is missed (e.g., by rotation of the camera around the polyp). The endoscopic capsule 100 according to the present embodiment comprises a power source 120, such as a battery, an RF transmitter 116 and an RF antenna 118. The length 122 of the endoscopic capsule may be within the range (both endpoints included) 10-40 mm, such as within 20-30 mm.

The diameter 124 of the endoscopic capsule may be within the range (both endpoints included) 1-20 mm, such as within 5-15 mm. The endoscopic capsule can include a receiver 160 for receiving machine learning algorithms from outside the endoscopic capsule, for detecting if there is a pathology in an image obtained in the one or more images from the first imaging system. A kit can include a receiver 162 with one or more antennas arranged for receiving images from said endoscopic capsule.

Figure 2:
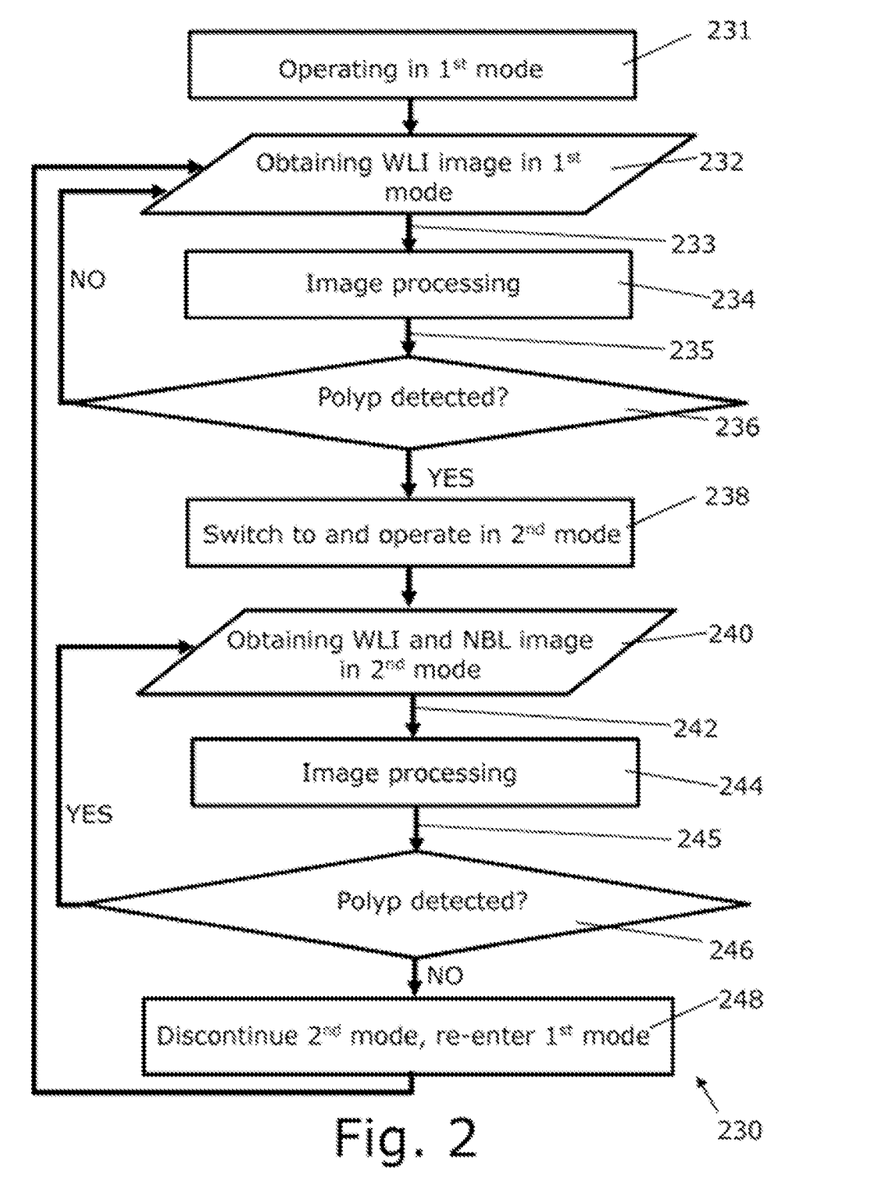
FIG. 2 is a flow-chart of a method according to the invention.

FIG. 2 is a flow-chart of a method according to the invention. More particularly, the figure shows a flow-chart of a method 230 of operating an endoscopic capsule 100, such as a pre-delivered (pre-swallowed) endoscopic capsule 100, wherein said method comprises:
operating 231 the endoscopic capsule in the first mode,
obtaining 232 one or more images 233 with the first imaging system,
accessing 234 with the processor the one or more images 233 from the first imaging system, such as accessing and image analysing so as to obtain a quantification of likelihood 235 that the image comprises a polyp 104,
detecting 236 if there is a polyp 104 in the one or more images from the first imaging system, such as determining if the likelihood 235 is above a predetermined threshold, and
switching 238 from the first mode to the second mode if a polyp 104 is detected in the one or more images from the first imaging system.

In the present embodiment, the method further comprises:
operating 238 the endoscopic capsule in the second mode,
obtaining 240 one or more images 242 with the first imaging system,
accessing 244 with the processor the one or more images 242 from the first imaging system, such as accessing and image analysing so as to obtain a quantification of likelihood 245 that the image comprises a polyp 104,
detecting 246 if there is a polyp 104 in the one or more images from the first imaging system, such as determining if the likelihood 245 is above a predetermined threshold, and
switching 248 from the second mode to the first mode if a polyp 104 is not detected in the one or more images from the first imaging system.

In the present embodiment, the method further comprises:
operating 238 the endoscopic capsule 100 in the second mode,
obtaining 240 one or more images with the second imaging system, and
transmitting one or more images obtained in the second mode to a database.

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. An endoscopic capsule (100) comprising:
a first imaging system (101, 110, 112),
a second imaging system (102, 110, 112), wherein the first imaging system is arranged for obtaining images at a broader spectral range than the second imaging system, and
a processor (114), wherein the endoscopic capsule is arranged for operating in any one of:
a first mode wherein a frame rate of the first imaging system (101, 110, 112) is higher than a frame rate of the second imaging system (102, 110, 112), and
a second mode wherein the frame rate of the second imaging system is higher than the frame rate of the second imaging system in the first mode, wherein the processor (114) in the first mode is arranged for:
accessing one or more images from the first imaging system (101, 110, 112),
detecting if there is a polyp (104) in the one or more images from the first imaging system (101, 110, 112), and
switching from the first mode to the second mode if a polyp (104) is detected, by a machine learning algorithm employed in the processor, in the one or more images from the first imaging system (101, 110, 112).

2. The endoscopic capsule (100) according to claim 1, wherein the endoscopic capsule (100) is further arranged for transmitting images outside the endoscopic capsule from the first and/or second mode, wherein a polyp (104) is detected.

3. The endoscopic capsule (100) according to claim 1, wherein the first imaging system (101, 110, 112) is a white light imaging system.

4. The endoscopic capsule (100) according to claim 1, wherein the second imaging system (102, 110, 112) is a narrowband imaging system.

5. The endoscopic capsule (100) according to claim 1, further comprising one or more illumination systems (101, 102).

6. The endoscopic capsule (100) according to claim 1, comprising one or more illumination systems (101, 102), said illumination systems comprising a white light source and a narrowband imaging source.

7. The endoscopic capsule (100) according to claim 1, comprising one or more illumination systems (101, 102), said illumination systems comprising 6 light emitting diodes including 2 white light emitting diode, 2 green light emitting diodes, and 2 blue light emitting diodes.

8. The endoscopic capsule (100) according to claim 1, wherein the endoscopic capsule (100) further comprises a receiver for receiving machine learning algorithms from outside the endoscopic capsule, for detecting if there is a pathology in an image obtained in the one or more images from the first imaging system.

9. The endoscopic capsule (100) according to claim 1, wherein the endoscopic capsule is arranged so that a period of time covering:
obtaining with the first imaging system an image with a polyp,
detection of a polyp in the image with the polyp,
switching from the first mode to the second mode due to the detection of the polyp in the image with the polyp, and
obtaining with the second imaging system an image,
is equal to or less than 10 seconds.

10. The endoscopic capsule (100) according to claim 1, wherein the processor in the second mode is arranged for:
accessing one or more images from the first imaging system and/or the second imaging system, detecting and/or confirming if there is a polyp in the one or more images from the first imaging system and/or the second imaging system, and
the processor is furthermore arranged for switching from the second mode to the first mode if a polyp is not detected in the one or more images from the first imaging system.

11. The endoscopic capsule (100) according to claim 1, wherein the endoscopic capsule is also arranged for quantifying bowel cleanliness.

12. A kit comprising:
the endoscopic capsule (100) according to claim 1,
an optional transmitter for transmitting one or more instructions, said instructions comprising a machine learning algorithms to the endoscopic capsule, and
a receiver with one or more antennas arranged for receiving images from said endoscopic capsule.

13. A system comprising:
the endoscopic capsule (100) according to claim 1,
an optional database of machine learning algorithms suitable for transmitting one or more machine learning algorithms to the endoscopic capsules, and
a database suitable for storing images obtained in the second mode.

14. A method (230) of operating a swallowed endoscopic capsule (100), according to claim 1, wherein said method comprises:
operating (231) the endoscopic capsule in the first mode,
obtaining (232) one or more images (233) with the first imaging system (101, 110, 112),
accessing (234) with the processor the one or more images (233) from the first imaging system (101, 110, 112),
detecting (236) if there is a polyp (104) in the one or more images from the first imaging system (101, 110, 112),
switching (238) from the first mode to the second mode if a polyp (104) is detected in the one or more images from the first imaging system (101, 110, 112).

15. The method of operating the endoscopic capsule (100) according to claim 14, wherein the method further comprises:
operating (238) the endoscopic capsule in the second mode,
obtaining (240) one or more images (242) with the first imaging system,
accessing (244) with the processor the one or more images (242) from the first imaging system,
detecting (246) if there is a polyp (104) in the one or more images from the first imaging system, and
switching (248) from the second mode to the first mode if a polyp (104) is not detected in the one or more images from the first imaging system.

16. The method of operating the endoscopic capsule (100) according to claim 14, wherein the method further comprises,
- operating (238) the endoscopic capsule (100) in the second mode,
- obtaining (240) one or more images with the second imaging system (102, 110, 112), and
- transmitting one or more images obtained in the second mode to a database.

17. The method of operating an endoscopic capsule (100) according to claim 14, wherein the method further comprises transmitting one or more instructions, said instructions comprising one or more machine learning algorithms, to the endoscopic capsule (100) before:
- operating (231) the endoscopic capsule in the first mode,
- obtaining (232) one or more images (233) with the first imaging system (101, 110, 112),
- accessing (234) with the processor the one or more images (233) from the first imaging system (101, 110, 112),
- detecting (236) if there is a polyp (104) in the one or more images from the first imaging system (101, 110, 112), and
- switching (238) from the first mode to the second mode if a polyp (104) is detected in the one or more images from the first imaging system (101, 110, 112).

18. A use of the endoscopic capsule (100) according to claim 1, comprising obtaining a set of a plurality of images from any of the first and the second image systems and/or first and second modes and optionally transmitting a subset of said set of the plurality of images.

* * * * *